United States Patent [19]

Konno et al.

[11] Patent Number: 5,587,510

[45] Date of Patent: Dec. 24, 1996

[54] (S)-2-ARALKYL-3-CHLOROPROPIONIC ACID AND PROCESS FOR THE PREPARATION THEREOF

[75] Inventors: Masao Konno; Yoshifumi Yuasa, both of Kanagawa, Japan

[73] Assignee: Takasago International Corporation, Tokyo, Japan

[21] Appl. No.: 448,310

[22] Filed: May 23, 1995

[30] Foreign Application Priority Data

May 25, 1994 [JP] Japan .................................. 6-133924

[51] Int. Cl.⁶ .................................................. C07C 53/134
[52] U.S. Cl. .................................................. 562/496
[58] Field of Search ............................................. 562/496

[56] References Cited

PUBLICATIONS

CA 112:157903 (1990).
*Chemische. Berichte*, 123 (1990), pp. 635–638.

*Primary Examiner*—Paul J. Killos
*Attorney, Agent, or Firm*—Sughrue, Mion, Zinn, Macpeak & Seas

[57] ABSTRACT

The present invention provides a novel 2-aralkyl-3-chloropropionic acid and a process for the preparation thereof. A novel 2-aralkyl-3-chloropropionic acid is represented by the general formula (1):

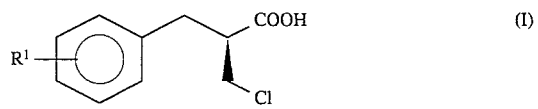

and can be prepared by asymmetrically hydrogenating a (Z)-2-aralkylidene-3-chloropropionic acid represented by the general formula (II):

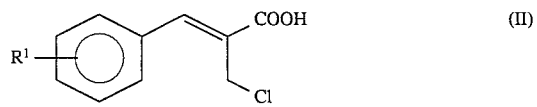

with a complex of a bidentate phosphine with ruthenium as a catalyst in the presence of a tertiary amine.

5 Claims, No Drawings

(S)-2-ARALKYL-3-CHLOROPROPIONIC ACID AND PROCESS FOR THE PREPARATION THEREOF

FIELD OF THE INVENTION

The present invention relates to a (S)-2-aralkyl-3chloropropionic acid and a process for the preparation thereof.

BACKGROUND OF THE INVENTION

One of anodynes which have been recently developed is an enkephalinase inhibitor. The structure of such an enkephalinase inhibitor contains a moiety derived from 2-aralkyl-3-acetylthiopropionic acid. It has been known that enkephalinase inhibitors exert different pharmacological actions depending on the steric structure of the aralkyl group in the 2-position. It has also been known that enkephalinase inhibitors having an aralkyl group in (S) configuration exert effective pharmacological actions.

An example of the process for the preparation of a (S)-2-aralkyl-3-acetylthiopropionic acid is an optical resolution method with ephedrine as disclosed in JP-A-2-161 (The term "JP-A" as used herein means an "unexamined published Japanese patent application").

However, the optical resolution method which comprises directly obtaining a (S)-2-aralkyl-3-acetylthiopropionic acid is disadvantageous in that a very expensive optical resolution agent must be used.

On the other hand, one possible 2-aralkyl-3-acetylthiopropionic acid precursors is a 2-aralkyl-3-halogenopropionic acid. An example of the process for the preparation of an optically active 2-aralkyl-3-halogenopropionic acid is a process for the preparation of a (R)-2-benzyl-3-chloropropionic acid and the methyl ester thereof as disclosed in K. Haaf et al., *Chemische. Berichte,* 123 (1990), pp. 635–638. In the preparation process disclosed in this reference, L-phenylalanine is processed in 7 stages including high temperature rearrangement reaction and 10 enzymatic reaction with lipase derived from pig liver to synthesize a (R)-2-benzyl-3-chloropropionic acid.

However, the product is not in (S)-configuration and is produced through complicated steps.

As the process for the preparation of a (S)-2-aralkyl-3-acetylthiopropionic acid or (R)-2-aralkyl-3-chloropropionic acid as an intermediate of an enkephalinase inhibitor there have been known the foregoing processes. However, these processes are not industrially satisfiable because they require a multi-stage reaction and expensive reagents.

SUMMARY OF THE INVENTION

It is therefore an object of the present invention to provide a (S)-2-aralkyl-3-chloropropionic acid represented by the following general formula (I):

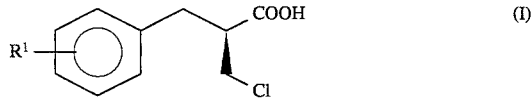

wherein $R^1$ represents a hydrogen atom or a lower alkyl group as a novel compound and an industrially advantageous process for the preparation thereof.

Under these circumstances, the inventors made extensive studies. As a result, it was found that the asymmetrical hydrogenation of a (Z)-2-aralkylidene-3-chloropropionic acid with a complex of ruthenium with an optically active bidentate phosphine provides a (S)-2-aralkyl-3-chloropropionic acid as a novel high optical purity compound in a high yield. Thus, the present invention.

The present invention provides a process for the preparation of a (S)-2-aralkyl-3-chloropropionic acid, as a novel compound, represented by the general formula (I):

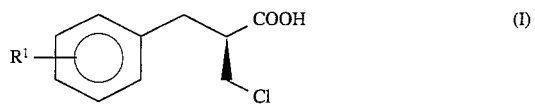

wherein $R^1$ represents a hydrogen atom or a lower alkyl group, which comprises asymmetrically hydrogenating a (Z) -2-aralkylidene- 3-chloropropionic acid represented by the general formula (II):

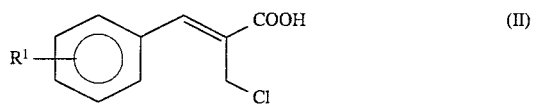

wherein $R^1$ is as defined above, with a complex of a bidentate phosphine represented by the general formula (III):

wherein $R^2$, $R^3$, $R^4$ and $R^5$ may be the same or different and each represent a phenyl group, a cyclohexyl group, a cyclopentyl group, or a substituted phenyl group substituted with a lower alkyl group, a lower alkoxy group or a halogen atom; and A is represented by the general formula (IV) or (V):

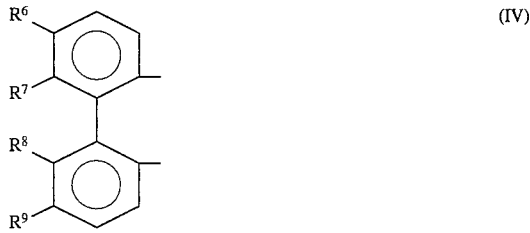

wherein $R^6$ and $R^9$ each represent a hydrogen atom; and $R^7$ and $R^8$ each represent a methyl group; or $R^6$ forms a tetramethylene group with $R^7$ and $R^8$ forms another tetramethylene group with $R^9$:

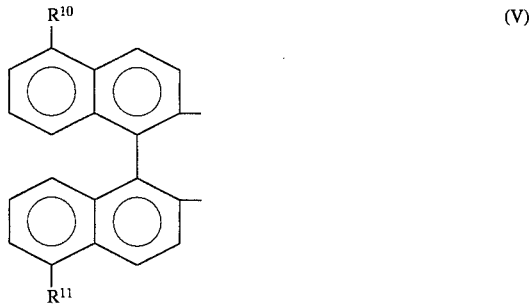

wherein $R^{10}$ and $R^{11}$ may be the same or different and each represent a hydrogen atom, an amino group, an acetylamino group, or $-SO_3M$ (in which M represents a hydrogen atom or an alkali metal atom), with ruthenium as a catalyst, in the presence of a tertiary amine represented by the general formula (VI):

wherein $R^{12}$, $R^{13}$ and $R^{14}$ may be the same or different and each represent a lower alkyl group. The present invention also provides the foregoing novel compound.

DETAILED DESCRIPTION OF THE INVENTION

The present invention will be further described hereinafter.

In the present invention, the lower alkyl group represents a $C_{1-4}$ straight-chain or branched alkyl group. Specific examples of such an alkyl group include methyl group, ethyl group, n-propyl group, isopropyl group, n-butyl group, isobutyl group, sec-butyl group, and tert-butyl group. The lower alkoxy group represents a $C_{1-4}$ straight-chain or branched alkoxy group. Specific examples of such an alkoxy group include methoxy group, ethoxy group, n-propoxy group, isopropoxy group, n-butoxy group, isobutoxy group, sec-butoxy group, and tert-butoxy group. Specific examples of the halogen atom include chlorine atom, bromine atom, iodine atom, and fluorine atom.

The novel (S)-2-aralkyl-3-chloropropionic acid is represented by the general formula (I). When $R^1$ is a lower alkyl group, its substitution position may be any of o-position, m-position and p-position. Particularly preferred examples of such a (S)-2-aralkyl-3-chloropropionic acid include (S)-2-benzyl-3-chloropropionic acid, and (S)-2-p-tolyl-3-chloropropionic acid.

The preparation of such a (S)-2-aralkyl-3-chloropropionic acid of the present invention can be accomplished by asymmetrically hydrogenating a (Z)-2-aralkylidene-3-chloropropionic acid with a complex of ruthenium with an optically active bidentate phosphine as a catalyst in the presence of a tertiary amine.

A (Z)-2-aralkylidene-3-chloropropionic acid represented by the general formula (II) as a starting material of (S)-2-aralkyl-3-chloropropionic acid can be obtained by any known method as disclosed in *J. Chem. Soc. Perkin Trans.* I, 2293 (1983). In some detail, it can be prepared by a process which comprises allowing an acrylic ester to be condensed with an aromatic aldehyde such as benzaldehyde in the presence of 1,4-diazabicyclo[2,2,2]octane or the like to produce an ester, 3-hydroxy-2-methylene-3-arylpropionate, and then allowing hydrochloric acid to act on the ester 3-hydroxy-2-methylene-3-arylpropionate in the presence of sulfuric acid to produce an ester, (Z)-2-aralkylidene-3-chloropropionate, which is then hydrolyzed.

The (Z)-2-aralkylidene-3-chloropropionic acid represented by the general formula (II) thus obtained may be asymmetrically hydrogenated with a complex of ruthenium with an optically active bidentate phosphine as a catalyst in the presence of a tertiary amine to obtain a (S)-2-aralkyl-3-chloropropionic acid represented by the general formula (I) as a compound of the present invention.

Preferred examples of the complex of ruthenium with an optically active phosphine to be used as a catalyst include complexes represented by the following general formulae (VII) to (X):

(1) Complexes represented by the following formula (VII):

wherein L represents a bidentate phosphine represented by the general formula (III):

wherein $R^2$, $R^3$, $R^4$, $R^5$ and A are as defined above; and S is represented by the general formula (VI):

$$NR^{12}R^{13}R^{14} \qquad (VI)$$

wherein $R^{12}$, $R^{13}$ and $R^{14}$ are as defined above, with the proviso that when y is 0, x is 2, z is 4 and p is 1, and when y is 1, x is 1, z is 1 and p is 0.

(2) Complexes represented by the general formula (VIII):

wherein $R^{15}$ represents a lower alkyl group or a trifluoromethyl group; and L is as defined above.

(3) Complexes represents by the following general formula (IX):

wherein X represents a halogen atom; and L is as defined above.

(4) Complexes represented by the general formula (X):

wherein X represents a halogen atom; J represents benzene, p-cymene, a lower alkyl ester of benzoic acid or acetonitrile; Q represents a halogen atom, $ClO_4$, $PF_6$ or $BF_4$; and L is as defined above, with the proviso that when J is benzene, p-cymene or a lower alkyl ester of benzoic acid, k is 1, m is 1 and n is 1, and when J is acetonitrile, m is 1 and n is 1 if k is 1, or m is 4 and n is 2 if k is 0.

Examples of the ruthenium compound as a starting material of the foregoing complexes include $[RuCl_2(COD)]_n$ (in which COD herein represents 1,5-cyclooctadiene, and n represents a natural number), $[RuBr_2(COD)]_n$, $[RuCl_2(NBD)]_n$ (in which NBD herein represents norbornadiene), $[RuBr_2(NBD)]_n$, $[RuCl_2(benzene)]_2$, $[RuBr2(benzene)]_2$, $[RuI_2(benzene)]_2$, $[RuCl_2(p\text{-cymene})]_2$, $[RuBr_2(p\text{-cymene})]_2$, and $[RuI_2(p\text{-cymene})]_2$.

Specific examples of the optically active bidentate phosphine as another starting material of the foregoing complexes include the following compounds.

The following optically active bidentate phosphines can be divided into two groups, i.e., those having (+) optical rotation and those having (−) optical rotation. However, such an indication will be omitted.

2,2'-Bis(diphenylphosphino)-6,6'-dimethylbiphenyl (hereinafter referred to as "bip"), 2,2'-bis(di(p-tolyl)phosphino)-6,6'-dimethylbiphenyl (hereinafter referred to as "T-bip"), 2,2'-bis(di(p-tert-butylphenyl)phosphino)-6,6'-dimethylbiphenyl (hereinafter referred to as "Bu-bip"), 2,2'-bis(di(p-methoxyphenyl)phosphino)-6,6'-dimethylbiphenyl (hereinafter referred to as "MeO-bip"), 2,2'-bis(di(p-chlorophenyl)phosphino)-6,6'-dimethylbiphenyl (hereinafter referred to as "Cl-bip"), 2,2'-bis(diphenylphosphino)-5,5', 6,6', 7,7', 8,8'-octahydro-1,1'-binaphthyl (hereinafter referred to as "OcH"), 2,2'-bis(di(p-tolyl)phosphino)-5,5', 6,6', 7,7', 8,8'-octahydro-1,1'-binaphthyl (hereinafter referred to as "T-OcH"), 2,2'-bis(di(p-tertbutylphenyl)phosphino)-5,5', 6,6', 7,7', 8,8'-octahydro-1,1'-binaphthyl (hereinafter referred to as "Bu-OcH"), 2,2'-bis(di(p-methoxyphenyl)phosphino)-5,5', 6,6', 7,7', 8,8'-octahydro-1,1'- binaphthyl (hereinafter referred to as "MeO-OcH"), 2,2'-bis(di(p-chlorophenyl)phosphino)-5,5', 6,6', 7,7', 8,8'-octahydro-1,1'-binaphthyl (hereinafter referred to as "Cl-OcH"), 2,2'-bis(diphenylphosphino)-1,1'binaphthyl (hereinafter referred to as "bin"), 2,2'-bis(di(p-tolyl)phosphino)-1,1'-binaphthyl (hereinafter referred to as "T-bin"), 2,2'-bis(di(p-tert-butylphenyl)phosphino)-1,1'-binaphthyl (hereinafter referred to as "Bu-bin"), 2,2'bis(di(3,5-xylyl)phosphino)-1,1'-binaphthyl (hereinafter referred to as "Xy-bin"), 2,2'-bis(di(p-methoxyphenyl) phosphino)-1,1'-binaphthyl (hereinafter referred to as "MeO-bin"), 2,2'-bis(di(p-chlorophenyl)phosphino-1,1'-binaphthyl (hereinafter referred to as "Cl-bin"), 2,2'-bis(di(cyclohexyl)phosphino)-1,1'-binaphthyl (hereinafter referred to as "Cy-bin"), 2,2'-bis(di(cyclopentyl)phosphino)-1,1'-binaphthyl (hereinafter referred to as "Cp-bin"), 2,2'-bis(diphenylphosphino)-5,5'-diamino-1,1'-binaphthyl (hereinafter referred to as "NH-bin"), 2,2'-bis(diphenylphosphino)-5,5'-di(acetylamino)-1,1'-binaphthyl (hereinafter referred to as "Ac-bin"), 2,2'-bis(diphenylphosphino)-5,5'-disulfo-1,1'-binaphthyl (hereinafter referred to as "SO-bin"), and disodium 2,2'-bis(diphenylphosphino)-1,1'-binaphthyl-5,5'-disulfonate (hereinafter referred to as "SNa-bin").

The complex to be used in the present invention may be formed by an optically active bicentate phosphine and a ruthenium compound.

Optically active bidentate phosphines can be divided into two groups i.e., those having (+) optical rotation and those having (−) optical rotation. However, such an indication will be omitted.

RuHCl(Bu-bip)$_2$, RuHCl(T-bip)$_2$, RuHCl(Bu-bip)$_2$, RuHCl(MeO-bip)$_2$, RuHCl(Cl-bip)$_2$, RuHCl(OcH)$_2$, RuHCl(T-OcH)$_2$, RuHCl(Bu-OcH)$_2$, RuHCl(MeO-OcH)$_2$, RuHCl(Cl-OcH)$_2$, RuHCl(bin)P$_2$, RuHCl(T-bin)$_2$, RuHCl(Bu-bin)$_2$, RuHCl(MeO-bin)$_2$, RuHCl(Cl-bin)$_2$, RuHCl(Xy-bin)$_2$, RuHCl(Cy-bin)$_2$, RuHCl(Cp-bin)$_2$, RuHCl(NH-bin)$_2$, RuHCl(Ac-bin)$_2$, RuHCl(SO-bin)$_2$, RuHCl(SNa-bin)$_2$, Ru$_2$Cl$_4$(bip)$_2$(NEt$_3$), Ru$_2$Cl$_4$(Bu-bip)$_2$(NEt$_3$), Ru$_2$Cl$_4$(MeO-biP)$_2$(NEt$_3$), Ru$_2$Cl$_4$(Cl-bip)$_2$(NEt$_3$), Ru$_2$Cl$_4$(OcH)$_2$(NEt$_3$), Ru$_2$Cl$_4$(T-OcH)$_2$NEt$_3$), Ru$_2$Cl$_4$(Bu-OcH)$_2$(NEt$_3$), Ru$_2$Cl$_4$(MeO-OcH)$_2$(NEt$_3$)$_2$, Ru$_2$Cl$_4$(Cl-OcH)$_2$(NEt$_3$), Ru$_2$Cl$_4$(bin)$_2$(NEt$_3$), Ru$_2$Cl$_4$(T-bin)$_2$(NEt$_3$), Ru$_2$Cl$_4$(Bu-bin)$_2$(NEt$_3$), Ru$_2$Cl$_4$(MeO-bin)$_2$(NEt$_3$), Ru$_2$Cl$_4$(Cl-bin)$_2$(NEt$_3$), Ru$_2$Cl$_4$(Xy-bin)$_2$(NEt$_3$), Ru$_2$Cl$_4$(CY-bin)$_2$(NEt$_3$), Ru$_2$Cl$_4$(Cp-bin)$_2$(NEt$_3$), Ru$_2$Cl$_4$(NH-bin)$_2$(NEt$_3$), Ru$_2$Cl$_4$(Ac-bin)$_2$(NEt$_3$), Ru$_2$Cl$_4$(SO-bin)$_2$(NEt$_3$), Ru$_2$Cl$_4$(SNa-bin)$_2$(NEt$_3$), Ru(OCOCH$_3$)$_2$(bip), Ru(OCOCH$_3$)$_2$(T-bip), Ru(OCOCH$_3$)$_2$(Bu-bip), Ru(OCOCH$_3$)$_2$(MeO-bip), Ru(OCOCH$_3$)$_2$(Cl-bip), Ru(OCOCH$_3$)$_2$(OcH), Ru(OCOCH$_3$)$_2$(T-OcH), Ru(OCOCH$_3$)$_2$(Bu-OcH), Ru(OCOCH$_3$)$_2$(MeO-OcH), Ru(OCOCH$_3$)$_2$(Cl-OcH), Ru(OCOCH$_3$)$_2$(bin), Ru(OCOCH$_3$)$_2$(T-bin), Ru(OCOCH$_3$)$_2$(Bu-bin), Ru(OCOCH$_3$)$_2$(MeO-bin), Ru(OCOCH$_3$)$_2$(Cl-bin), Ru(OCOCH$_3$)$_2$(Xy-bin), Ru(OCOCH$_3$)$_2$(Cy-bin), Ru(OCOCH$_3$)$_2$(Cp-bin), Ru(OCOCH$_3$)$_2$(NH-bin), Ru(OCOCH$_3$)$_2$(Ac-bin), Ru(OCOCH$_3$)$_2$(SO-bin), Ru(OCOCH$_3$)$_2$(SNa-bin), Ru(OCOCF$_3$)$_2$(bip), Ru(OCOCF$_3$)$_2$(T-bip), Ru(OCOCF$_3$)$_2$(Bu-bip), Ru(OCOCF$_3$)$_2$(MeO-bip), Ru(OCOCF$_3$)$_2$(Cl-bip), Ru(OCOCF$_3$)$_2$(OcH), Ru(OCOCF$_3$)$_2$(T-OcH), Ru(OCOCF$_3$)$_2$(Bu-OcH), Ru(OCOCF$_3$)$_2$(MeO-OcH ), Ru(OCOCF$_3$)$_2$(Cl-OcH), Ru(OCOCF$_3$)$_2$(bin), Ru(OCOCF$_3$)$_2$(T-bin), Ru(OCOCF$_3$)$_2$(Bu-bin), Ru(OCOCF$_3$)$_2$(MeO-bin), Ru(OCOCF$_3$)$_2$(Cl-bin), Ru(OCOCF$_3$)$_2$(Xy-bin), Ru(OCOCF$_3$)$_2$(Cy-bin), Ru(OCOCF$_3$)$_2$(Cp-bin), Ru(OCOCF$_3$)$_2$(NH-bin), Ru(OCOCF$_3$)$_2$(Ac-bin), Ru(OCOCF$_3$)$_2$(SO-bin), Ru(OCOCF$_3$)$_2$(SNa-bin), Ru(OCOBu-t)$_2$(bip), Ru(OCOBu-t)$_2$(T-bip), Ru(OCOBu-t)$_2$(Bu-bip), Ru(OCOBu-t)$_2$(MeO-bip), Ru(OCOBu-t)$_2$(Cl-bip), Ru(OCOBu-t)$_2$(OcH), Ru(OCOBu-t)$_2$(T-OcH), Ru(OCOBu-t)$_2$(Bu-OcH), Ru(OCOBu-t)$_2$(MeO-OcH), Ru(OCOBu-t)$_2$(Cl-OcH), Ru(OCO-But)$_2$(bin), Ru(OCOBu-t)$_2$(T-bin), Ru(OCOBu-t)$_2$(Bu-bin), Ru(OCO-Bu-t)$_2$(MeO-bin), Ru(OCOBu-t)$_2$(Cl-bin), Ru(OCOBu-t)$_2$(Xy-bin), Ru(OCOBu-t)$_2$(Cy-bin), Ru(OCOBu-t)$_2$(Cp-bin), Ru(OCOBu-t)$_2$(NH-bin), Ru(OCOBu-t)$_2$(Ac-bin), Ru(OCOBu-t)$_2$(SO-bin), Ru(OCO-But)$_2$(SNa-bin), RuCl$_2$(bip), RuCl$_2$(T-bip), RuCl$_2$(Bu-bip), RuCl$_2$(MeO-bip), RuCl$_2$(Cl-bip), RuCl$_2$(OcH), RuCl$_2$(T-OcH), RuCl$_2$(Bu-OcH), RuCl$_2$(MeO-OcH), RuCl$_2$(Cl-OcH), $_{RuCl2}$(bin), RuCl$_2$(T-bin), RuCl$_2$(Bu-bin), RuCl$_2$(MeO-bin), RuCl$_2$(Cl-bin), RuCl$_2$(Xy-bin), RuCl$_2$(Cy-bin), RuCl$_2$(Cp-bin), RuCl$_2$(NH-bin), RuCl$_2$(Ac-bin), RuCl$_2$(SO-bin), RuCl$_2$(SNa-bin), RuBr$_2$(bip), RuBr$_2$(T-bip), RuBr$_2$(Bu-bip), RuBr$_2$(MeO-bip), RuBr$_2$(Cl-bip), RuBr$_2$(OcH), RuBr$_2$(T-OcH), RuBr$_2$(Bu-OcH), RuBr$_2$(MeO-OcH), RuBr$_2$(Cl-OcH), RuBr$_2$(bin), RuBr$_2$(T-bin)$_)$, RuBr$_2$(Bu-bin), RuBr$_2$(MeO-bin), RuBr$_2$(Cl-bin), RuBr$_2$(Xy-bin), RuBr$_2$(Cy-bin), RuBr$_2$(Cp-bin), RuBr$_2$(NH-bin), RuBr$_2$(Ac-bin), RuBr$_2$(SO-bin), RuBr$_2$(SNa-bin), [RuCl(benzene)(bip)]Cl, [RuI(p-cymene)(T-bip)]I, [RuBr(benzene)(Bu-bip)]Br, [RuCl(Me-Ar)(MeO-bip)]Cl (Me-Ar hereinafter stands for methyl benzoate), [RuCl(benzene)(Cl-bip)]Cl, [RuI(benzene)(OcH)]I, [RuCl(benzene)(T-OcH)]Cl, [RuCl(P-cymene)(Bu-OcH)]Cl [RuBr(benzene)(MeO-OcH)]Br, [RuCl(benzene)(Cl-OcH)Cl, [RuI(p-cymene)(bin)]I, [RuCl(benzene)(T-bin)]Cl, [RuI(Me-Ar)(Bu-bin)]I, [RuBr(benzene)(MeO-bin)]Br, [RuCl(P-cymene)(Cl-bin)]Cl, [RuI(benzene)(Xy-bin)]I, [RuCl(benzene)(Cy-bin)]Cl, [RuI(Me-Ar)(Cp-bin)]I, [RuCl(benzene)(NH-bin)]Cl, [RuCl(benzene)(Ac-bin)]Cl, [RuBr(benzene)(SO-bin)]Br, [RuCl(p-cymene)(SNa-bin )]Cl, [RuCl(benzene)(bip)]ClO$_4$, [RuCl(p-cymene)(T-bip)]ClO$_4$, [RuCl(benzene)(Bu-bip)]ClO$_4$, [RuCl(Me-Ar)(MeO-bip)]ClO$_4$, [RuCl(benzene)(Cl-bip)]ClO$_4$, [RuCl(benzene)(OcH)]ClO$_4$, [RuCl(benzene)(T-OcH)]ClO$_4$, [RuCl(p-cymene)(Bu-OcH)]ClO$_4$, [RuCl(benzene)(MeO-OcH)]ClO$_4$, [RuCl(benzene)(Cl-OcH)]ClO$_4$, [RuCl(p-cymene)(bin)]ClO$_4$, [RuCl(benzene)(T-bin)]ClO$_4$, [RuCl(Me-Ar)(Bu-bin)]ClO$_4$, [RuCl(benzene)(MeO-bin)]ClO$_4$, [RuCl(p-cymene)(Cl-bin)]ClO$_4$, [RuCl(benzene)(Xy-bin)]ClO$_4$, [RuCl(benzene)(Cy-bin)]ClO$_4$, [RuCl(Me-Ar)(Cp-bin)]ClO$_4$, [RuCl(benzene)(NH-bin)]ClO$_4$, [RuCl(benzene)(Ac-bin)]ClO$_4$, [RuCl(benzene)(SO-bin)]ClO$_4$, [RuCl(p-cymene) (SNa-bin)]ClO$_4$, [RuCl(CH$_3$CN)$_2$(bip)]Cl, [RuCl(CH$_3$CN)$_2$(T-bip)]Cl, [RuCl(CH$_3$CN)$_2$(Bu-bip)]Cl, [RuCl(CH$_3$CN)$_2$(MeO-bip)]Cl, [RuCl(CH$_3$CN)$_2$(Cl-bip)]Cl, [RuCl(CH$_3$CN)$_2$(OcH)]Cl, [RuCl(CH$_3$CN)$_2$(bin)]Cl, [RuCl(CH$_3$CN)$_2$(T-bin)]Cl, [RuCl(CH$_3$CN)$_2$(Cy-bin)]Cl, [Ru(CH$_3$CN)$_4$(bin)](ClO$_4$)2, [Ru(CH$_3$CN)$_4$(T-bin)](BF$_4$)$_2$, and [Ru(CH$_3$CN)$_4$(bin)](PF$_6$)$_2$.

These complexes may be prepared by, e.g., the following methods.

(i) Ru$_x$H$_y$Cl$_z$ (L)$_2$ (S)$_p$ type complex

The foregoing type of a complex can be prepared in accordance with methods as disclosed in T. Ikariya et al., *J. Chem. Soc., Chem. Commun.*, 922 (1985) and JP-A-61-63690. For example, the foregoing type of a complex wherein y is 0 can be obtained by reacting 1 molar equivalent of [RuCl$_2$(COD)]$_c$ (in which c represents a natural number) obtained by the reaction of ruthenium chloride with COD in an alcohol solvent such as ethanol with from 1.05 to 1.2 molar equivalents of a bidentate phosphine L in the presence of 4 molar equivalents of a tertiary amine such as triethylamine in a solvent such as toluene and ethanol.

On the other hand, the foregoing type of a complex wherein y is 1 can be prepared in the same manner as mentioned above except that the bidentate phosphine L is used in the molar amount of twice that of $[RuCl_2(COD)]_c$.

(ii) $Ru(OCOR^{15})_2$ (L) type complex

The foregoing type of a complex can be prepared in accordance with a method disclosed in JP-A-62-265293. For example, $Ru_2Cl_4(L)_2(NEt_3)$ obtained in the foregoing process (i) may be used as a starting material. The starting material is reacted with a lower carboxylate represented by $R^{15}COOM$ (in which $R^{15}$ and M are as defined above) in an alcohol solvent such as methanol, ethanol and tert-butanol at a temperature of from about 20° to 110° C. over from 3 to 15 hours. The solvent is then distilled off. The desired complex is extracted with a solvent such as ether and ethanol, and then dried to obtain a crude complex. The crude complex can be recrystallized from ethyl acetate or the like to obtain a purified product.

(iii) $RuX_2$ (L) type complex

The foregoing type of a complex can be prepared in accordance with a method disclosed in JP-A-63-145292. For example, $Ru_2Cl_4(L)_2(NEt_3)$ obtained in the foregoing process (i) and a salt represented by MQ (in which M and Q are as defined above) may be reacted with each other in a mixture of water and methylene chloride as a solvent with a quaternary ammonium salt or quaternary phosphonium salt, as a phase transfer catalyst, represented by the general formula (XI):

$$R^{16}R^{17}R^{18}R^{19}ZX \qquad (XI)$$

wherein $R^{16}$, $R^{17}$, $R^{18}$ and $R^{19}$ each represent a $C_{1-16}$ alkyl group, phenyl group or a benzyl group; Z represents a nitrogen atom or phosphorus atom; and X is as defined above. The amount of the salt MQ and the phase transfer catalyst are from 2 to 10 mol (preferably 5 mol) and from 1/100 to 1/10 mol per mole of ruthenium, respectively. The reaction may be effected at a temperature of from 5° to 30° C. over from 6 to 18 hours, normally 12 hours, with stirring.

Examples of the salt employable in this reaction include the perchlorate, borofluoride and hexafluorophosphate of sodium, potassium, lithium, etc. Examples of the phase transfer catalyst employable in this reaction include quaternary ammonium salts such as tetramethylammonium bromide, tetrapropylammonium bromide, tetrabutylammonium chloride, tetrabutylammonium iodide, octyltrimethylammonium bromide, lauryltrimethylammonium bromide, laurylt- riphenylammonium bromide, cetyltrimethylammonium chloride, methyltrioctylammonium chloride and benzyltriethylammonium bromide, and quaternary phosphonium salts corresponding to these quaternary ammonium salts.

(iv) $RuX_k J_m (L)Q_n$ type complex

The foregoing type of a complex can be prepared in accordance with a method as disclosed in JP-A-2-192189. For example, the foregoing type of a complex wherein J is benzene, p-cymene or a lower alkyl ester of benzoic acid can be obtained as follows. When both X and Q are chlorine atoms, $[RuCl_2J]_2$ may be used as a starting material. The starting material is reacted with a bidentate phosphine L in methanol, ethanol, benzene or methylene chloride, singly or in admixture, at a temperature of from 25° to 50° C. over from 30 minutes to 3 hours. The solvent is then distilled off under reduced pressure to obtain a $RuX_k J_m (L)Q_n$ type complex.

When both X and Q are bromine atoms or iodine atoms, $[RuCl_2J]_2$ as a starting material is reacted with a salt represented by MBr or MI (in which M is as defined above) in water, singly or in admixture with methylene chloride, as a solvent with a phase transfer catalyst represented by the general formula (XI) to obtain $[RuBr_2J]_2$ or $[RuI_2J]_2$. $[RuBr_2J]_2$ or $[RuI_2J]_2$ thus obtained is then reacted with a bidentate phosphine L in methanol, ethanol, benzene or methylene chloride, singly or in admixture, at a temperature of from 25° to 50° C. over from 30 minutes to 3 hours. The solvent is then distilled off under reduced pressure to obtain the desired complex.

When Q is a group other than a halogen atom, a complex such as [RuCl(J)(L)]Cl obtained as previously mentioned is dissolved in methanol, ethanol, acetone, methylene chloride or the like. To the solution is added a salt represented by MQ' (in which M is as defined above, and Q' represents $ClO_4$, $BPh_4$ or $PF_6$). The mixture is then stirred. The resulting small amount of insoluble matters are then filtered off. The filtrate is concentrated, and then dried to obtain the desired complex.

The foregoing type of a complex wherein J is acetonitrile can be prepared by a process which comprises dissolving a complex such as [RuCl(J)(L)]Cl obtained as previously mentioned in acetonitrile, refluxing the solution at a temperature of 50° C. over from 10 to 24 hours, distilling off excess acetonitrile, drying the residue, and then recrystallizing the resulting crude complex from methylene chloride to obtain $[RuCl(CH_3CN)_2(L)]Cl$.

An alternate process for the preparation of the foregoing type of a complex wherein J is acetonitrile comprises dissolving [RuCl(J)(L)]Cl complex, for example, in a mixture of acetonitrile and methanol, ethanol, acetone, methylene chloride or the like, adding MQ' (in which M and Q' are as defined above), stirring the mixture at a temperature of from 25° to 50° C. over from 10 to 24 hours, distilling off the solvent, drying the residue, and then recrystallizing the crude complex from methylene chloride to obtain a complex such as $[Ru(CH_3CN)_4(L)](ClO_4)_2$.

Referring further to the process for the preparation of the optically active carboxylic acid of the present invention, a (Z)-2-aralkylidene-3-chloroprionic acid is allowed to undergo reaction in the form of a solution in an alcohol such as methanol, ethanol and isopropyl alcohol, cyclic ether such as dioxane and tetrahydrofuran, aromatic hydrocarbon such as benzene and toluene, methylene chloride or ester such as methyl acetate and ethyl acetate, singly or in admixture, or a mixture thereof with water, in an autoclave. In this reaction, with a complex of ruthenium with an optically active bidentate phosphine added in an amount of from 1/500 to 1/10,000 mol, preferably from 1/500 to 1/1,000 mol per mol of the substrate, hydrogenation is effected at a hydrogen pressure of from 5 to 100 kg/cm², preferably from 20 to 50 kg/cm², at a temperature of from 10° to 50° C., preferably from 20° to 40° C., with stirring. The time required for reaction depends on the reaction temperature but is normally from 24 to 200 hours, preferably from 30 to 150 hours.

In the present invention, hydrogenation can be smoothly effected with a tertiary aliphatic amine as an auxiliary catalyst, e.g., trimethylamine, triethylamine, tri-n-propylamine, tri-n-butylamine, tripentylamine, preferably triethylamine, in an amount of from 1 to 4 mol per mol of the substrate. In the absence of such an auxiliary catalyst, the reaction proceeds little.

After the completion of the reaction, the solvent is distilled off. The residue is acidified with an acid such as hydrochloric acid, and then extracted with a proper organic solvent such as ethyl acetate. The solvent is then distilled off.

The resulting oily matter is then reacted with a primary amine such as cyclohexylamine to produce a salt. The salt is then recrystallized from an alcohol such as diisopropyl alcohol to obtain an optically pure (S)-2-aralkyl-3-chloropropionic acid.

The present invention will be further described in the following examples, but the present invention should not be construed as being limited thereto.

The physical properties hereinafter were measured by means of the following measuring instruments.

Measuring instruments

Conversion/selectivity:

Gas chromatography 5890 (available from Hewlett Packard Ltd.)

Column: silicon OV-1 (0.25 mm×25 m)(available from GL Science Inc.)

Temperature: raised 10° C. every minute between 100° C. and 220° C.

Infrared absorption spectrum (IR): Type IR-810 (available from JASCO Inc.)

Nuclear magnetic resonance spectrum ($^1$H-NMR): Type AM-400 (400 MHz) (available from Bruker Inc.)

Internal standard substance: tetramethylsilan

Optical rotation: Type DIP-4 polarimeter (available from JASCO Inc.)

EXAMPLE 1

(Synthesis of (S)-2-benzyl-3-chloropropionic acid)

(1) Synthesis of methyl 3-hydroxy-2-methylene-3-phenylpropionate 106 g (1 mol) of benzaldehyde (available from Nakarai Tesk K. K.), 11.2 g (0.1 mol) of 1,4-diazabicyclo[2,2,2]octane (available from Nacalai Tesque Inc.), and 90 ml (1 mol) of methyl acrylate (available from Nacalai Tesque Inc.) were stirred at room temperature over 7 days. To the reaction solution were then added 200 ml of a 6N hydrochloric acid and 200 ml of ethyl acetate so that an organic phase was extracted. The resulting organic phase was washed with a 10% brine, and then dried over magnesium sulfate. The solvent was then distilled off under reduced pressure. The residue was distilled under reduced pressure to obtain 167.8 g of the desired compound in the form of 99% purity colorless oily matter. When allowed to stand, the product was solidified. The product exhibited a melting point of from 34° to 36° C. (Yield: 87%)

Boiling point: 128° to 130° C. (187 Pa)

Nuclear magnetic resonance spectrum: $^1$H-NMR (δ; CDCl$_3$): 3.12 (1H, s), 3.69 (3H, s), 5.55 (1H, s), 5.83 (1H, s), 6.33 (1H, s), 7.29–7.37 (5H, m)

Infrared absorption spectrum: (νmax cm$^{-1}$;CHCl$_3$): 3325, 1720, 1635, 1600, 1500

(2) Synthesis of methyl (Z)-2-benzylidene-3-chloropropionate

To 50 g (0.26 mol) of methyl 3-hydroxy-2-methylene-3-phenylpropionate obtained in the process (1) were added dropwise 100 ml of a 35% hydrochloric acid under cooling with ice in 30 minutes. To the reaction mixture were then added dropwise 100 ml of a 98% sulfuric acid in 30 minutes. The reaction mixture was then stirred at room temperature overnight. After the completion of the reaction, the reaction solution was then poured into ice water. The reaction solution was then extracted with 200 ml of ethyl acetate. The resulting organic phase was washed with saturated aqueous solution of sodium bicarbonate and then with saturated brine, and then dried over magnesium sulfate. The solvent was then distilled off under reduced pressure. The residue was then distilled under reduced pressure to obtain 45.6 g (yield: 83% %) of the desired compound in the form of 96% purity colorless oily matter.

Boiling point: 134°–136° C. (80 Pa)

Nuclear magnetic resonance spectrum: $^1$H-NMR (δ; CDCl$_3$): 3.88 (3H, s), 4.48 (2H, s), 7.44–7.46 (3H, m), 7.54–7.56 (2H, m), 7.88 (1H, s)

Infrared absorption spectrum: (νmax cm$^{-1}$; neat): 1710, 1630, 1600, 1500

(3) Synthesis of (Z)-2-benzylidene-3-chloropropionic acid

Into a 500-ml pressure bottle were charged 40 g (0.19 mol) of methyl (Z)-2-benzylidene-3-chloropropionate, 150 ml of a 35% hydrochloric acid and 50 ml of acetic acid. The reaction mixture was then heated to a temperature of 100° C. with stirring overnight. After the completion of the reaction, the reaction solution was then poured into ice water. The reaction solution was then extracted with 200 ml of ethyl acetate. The resulting organic phase was washed with saturated brine, and then dried over magnesium sulfate. The solvent was then distilled off under reduced pressure. The resulting crude crystal was then recrystallized from a mixture of acetone and toluene to obtain 27.3 g (yield: 73%) of the desired compound in the form of colorless crystal. For the measurement of purity, the product was silylated with N,O-bis(trimethylsilyl)acetamide for gas chromatography. The result was 100%.

Melting point: 159 to 160° C.

Nuclear magnetic resonance spectrum: $^1$H-NMR (νCDCl$_3$): 4.50 (2H, s), 7.45–7.48 (3H, m), 7.59–7.62 (3H, m), 8.02 (1H, s)

Infrared absorption spectrum: (νmax cm$^{-1}$; CHCl$_3$): 1695, 1625, 1500

(4)(S)-2-benzyl-3-chloropropionic acid

Into a 1,000-ml autoclave were charged 30 g (0.153 mol) of (Z)-2-benzylidene-3-chloropropionic acid and 100 mg (0.11 mol) of Ru$_2$Cl$_4$((+)-T-bin)$_2$(Et$_3$N) in an atmosphere of nitrogen. The atmosphere in the autoclave was thoroughly replaced with nitrogen. To the reaction mixture were then added 300 ml of a 1:1 mixture of tetrahydrofuran and benzene and 30 ml of triethylamine in an atmosphere of nitrogen. The nitrogen atmosphere was then replaced with hydrogen to reach a hydrogen pressure of 35 kg/cm$^2$. The reaction mixture was then stirred at a temperature of 20° C. over 120 hours. After the completion of the reaction, the reaction mixture was partially silylated with N,O-bis(trimethylsilyl)acetamide for the measurement of conversion by gas chromatography. The results were 94% for conversion and 73% for selectivity. The reaction solution was then concentrated under reduced pressure. To the residue were then added 300 ml of a 5% hydrochloric acid. The resulting free oily matter was extracted with 300 ml of ethyl acetate, washed with saturated brine, and dried over magnesium sulfate. The solvent was then distilled off under reduced pressure to obtain 27.5 g of an oily matter.

The product was partially dissolved in a small amount of methylene chloride with the equivalent weight of 1-menthol and the catalytic amount of dimethylamino pyridine. The solution thus obtained was then acted on by the equivalent amount of 1-ethyl-3-(3-dimethylaminopropyl)carbodiimide so that it was 1-menthylesterified for the measurement of optical purity by gas chromatography. The result was 80% e.e. 27 g of the residual oily matter was then dissolved in 250 ml of ethanol. To the solution were then added 13.5 g of cyclohexylamine. The reaction mixture was then stirred over 10 minutes. The solvent was then distilled off. The resulting crude crystal was then recrystallized from isopropyl alcohol to obtain 20.1 g of a white crystal having a melting point of from 140° to 141° C. The amine salt thus obtained was then treated with a 5% hydrochloric acid to remove cyclohexylamine therefrom. Thus, 12.5 g (yield: 41%) of the desired compound was obtained in the form of viscous oily matter. For the measurement of optical purity, the product was 1-menthylesterified in the same manner as mentioned above for gas chromatography. The result was 100% e.e.

Optical rotation $[\alpha]D^{24}$: −5.75° (c=1.1, MeOH)

Nuclear magnetic resonance spectrum: $^1$H-NMR (δ; CDCl$_3$): 2.94–3.07 (3H, m), 3.08–3.16 (2H, m), 3.66–3.69 (2H, m), 7.21–7.32 (5H, m)

Infrared absorption spectrum: (νmax cm$^{-1}$; neat): 1710, 1600, 1500

EXAMPLES 2 TO 6

Processing was effected in the same manner as in Example 1 (4) except for solvent, temperature and time. The results are set forth in Table 1.

TABLE 1

| Example No. | Solvent | Temperature (°C.) | Time (hr) | Conversion (%) | Selectivity (%) | Optical yield (% e.e.) |
|---|---|---|---|---|---|---|
| Example 2 | MeOH | 20 | 140 | 85 | 73 | 34 |
| Example 3 | EtOH | 20 | 140 | 60 | 72 | 42 |
| Example 4 | THF | 20 | 116 | 93 | 66 | 57 |
| Example 5 | THF/benzene (1/1) | 35 | 140 | 100 | 56 | 70 |
| Example 6 | EtOAc/MeOH (1/1) | 35 | 140 | 100 | 55 | 51 |

EXAMPLE 7 AND COMPARATIVE EXAMPLE 1

In Example 7, tri-n-butylamine was used instead of triethylamine. In Comparative Example 1, processing was effected in the same manner as in Example 1 (4) except for reaction temperature and time in the case where no tertiary amine was added. The results are set forth in Table 2.

TABLE 2

| Example No. | Amine | Temperature (°C.) | Time (hr) | Conversion (%) | Selectivity (%) | Optical yield (% e.e.) |
|---|---|---|---|---|---|---|
| Comparative Example 1 | None | 35 | 48 | 4 | 0 | — |
| Example 7 | Tri-n-butylamine | 35 | 140 | 100 | 54 | 71 |

EXAMPLES 8 TO 10

Processing was effected in the same manner as in Example 1 (4) except that as the catalysts there were used Ru((−)-bin)(OCOCH$_3$)$_2$, RuI(p-cymene)((+)-bin)I, and RuCl$_2$((+)-bin), respectively, instead of Ru$_2$Cl$_4$((−)-T-bin)$_2$(Et$_3$N) and different reaction temperature and time conditions were used. The results are set forth in Table 3.

TABLE 3

| Example No. | Catalyst | Temperature (°C.) | Time (hr) | Conversion (%) | Selectivity (%) | Optical yield (% e.e.) |
|---|---|---|---|---|---|---|
| Example 8 | Ru((−)-bin)(OCOCH$_3$) | 40 | 48 | 63 | 73 | 64 |
| Example 9 | RuI(p-cymene)·((+)-T-bin)I | 35 | 48 | 100 | 45 | 30 |
| Example 10 | RuCl$_2$((+)-T-bin) | 35 | 48 | 52 | 70 | 68 |

The (S)-2-aralkyl-3-chloropropionic acid prepared according to the present invention is a novel compound. This product can be produced at a high optical purity on an industrial basis by asymmetrically hydrogenating a (Z)-2-aralkylidene-3-chloropropionic acid with a complex of an optically active bidentate phosphine with ruthenium as a catalyst. The (S)-2-aralkyl-3-chloropropionic acid thus obtained may be esterified by an ordinary method, and then acted on by an alkaline salt of thioacetic acid. Thus, a (S)-3-acetylthio-2-aralkylpropionic ester can be easily derived as an important intermediate of an enkephalinase inhibitor.

While the invention has been described in detail and with reference to specific embodiments thereof, it will be apparent to one skilled in the art that various changes and modifications can be made therein without departing from the spirit and scope thereof.

What is claimed is:

1. A process for the preparation of a (S)-2-aralkyl-3-chloropropionic acid represented by the general formula

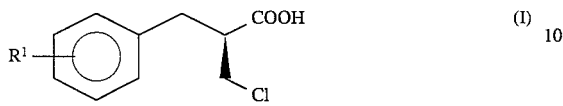

wherein $R^1$ represents a hydrogen atom or a lower alkyl group, which comprises asymmetrically hydrogenating a (Z)-2-aralkylidene-3-chloropropionic acid represented by the general formula (II):

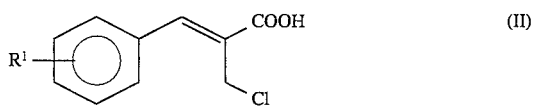

wherein $R^1$ is as defined above with a complex of a bidentate phosphine represented by the general formula (III):

wherein $R^2$, $R^3$, $R^4$ and $R^5$ may be the same or different and each represent a phenyl group, a cyclohexyl group, a cyclopentyl group, or a substituted phenyl group substituted with a lower alkyl group, a lower alkoxy group or a halogen atom; and A is represented by the general formula (IV) or (V):

wherein $R^6$ and $R^9$ each represent a hydrogen atom; and $R^7$ and $R^8$ each represent a methyl group; or $R^6$ forms a tetramethylene group with $R^7$, and $R^8$ forms an another tetramethylene group with $R^9$:

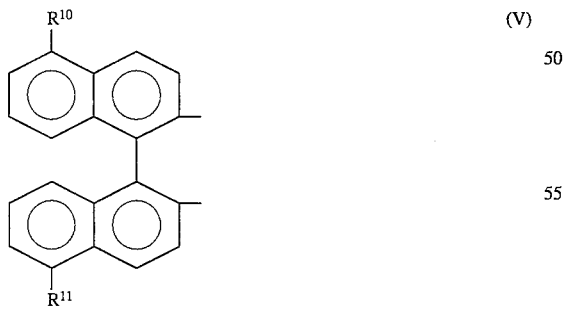

wherein $R^{10}$ and $R^{11}$ may be the same or different and each represent a hydrogen atom, an amino group, an acetylamino group, or —$SO_3M$ (in which M represents a hydrogen atom or an alkaline metal atom), with ruthenium as a catalyst, in the presence of a tertiary amine represented by the general formula (VI):

wherein $R^{12}$, $R^{13}$ and $R^{14}$ may be the same or different and each represent a lower alkyl group.

2. The process for the preparation of a (S)-2-aralkyl-3-chloropropionic acid as in claim 1, wherein said complex of a bidentate phosphine with ruthenium is a complex represented by the general formula (VII):

wherein L represents a bidentate phosphine represented by the general formula (III):

wherein $R^2$, $R^3$, $R^4$, $R^5$ and A are as defined in claim 1; and S is represented by the general formula (VI):

wherein $R^{12}$, $R^{13}$ and $R^{14}$ are as defined in claim 1, with the proviso that when y is 0, x is 2, z is 4, and p is 1 and when y is 1, x is 1, z is 1, and p is 0.

3. The process for the preparation of a (S)-2-aralkyl-3-chloropropionic acid as in claim 1, wherein said complex of a bidentate phosphine with ruthenium is a complex represented by the general formula (VIII):

wherein $R^{15}$ represents a lower aklyl group or a trifluoromethyl group; and L is a bidentate phosphine represented by the general formula (III):

wherein $R^2$, $R^3$, $R^4$ and $R^5$ may be the same or different and each represent a phenyl group, a cyclohexyl group, a cyclopentyl group, or a substituted phenyl group substituted with a lower alkyl group, a lower alkoxy group or a halogen atom; and A is represented by the general formula (IV) or (V):

wherein $R^6$ and $R^9$ each represent a hydrogen atom; and $R^7$ and $R^8$ each represent a methyl group; or $R^6$ forms a tetramethylene group with $R^7$, and $R^8$ forms another tetramethylene group with $R^9$;

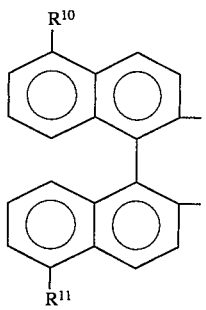

wherein $R^{10}$ and $R^{11}$ may be the same or different and each represent a hydrogen atom, an amino group, an acetylamino group, or —$S_3M$ (in which M represents a hydrogen atom or an alkali metal atom), with ruthenium as a catalyst, in the presence of a tertiary amine represented by the general formula (VI);

$$NR^{12}R^{13}R^{14} \quad (VI)$$

wherein $R^{12}$, $R^{13}$ and $R^{14}$ may be the same or different and each represent a lower alkyl group.

4. The process for the preparation of a (S)-2-aralkyl-3-chloropropionic acid as in claim 1, wherein said complex of a bidentate phosphine with ruthenium is a complex represented by the general formula (IX):

$$RuX_2(L) \quad (IX)$$

wherein X represents a halogen atom; and L is a bidentate phosphine represented by the general formula (III):

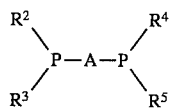

wherein $R^2$, $R^3$, $R^4$ and $R^5$ may be the same or different and each represent a phenyl group, a cyclohexyl group, a cyclopentyl group, or a substituted phenyl group substituted with a lower alkyl group, a lower alkoxy group or a halogen atom; and A is represented by the general formula (IV) or (V):

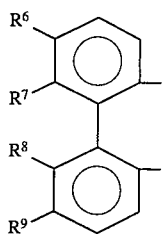

wherein $R^6$ and $R^9$ each represent a hydrogen atom; and $R^7$ and $R^8$ each represent a methyl group; or $R^6$ forms a tetramethylene group with $R^7$, and $R^8$ forms another tetramethylene group with $R^9$;

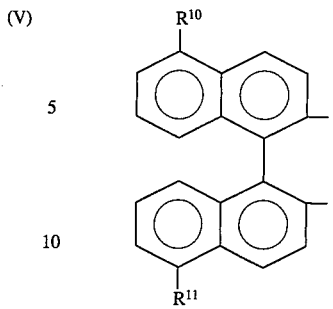

wherein $R^{10}$ and $R^{11}$ may be the same or different and each represent a hydrogen atom, an amino group, an acetylamino group, or —$SO_3M$ (in which M represents a hydrogen atom or an alkali metal atom), with ruthenium as a catalyst, in the presence of a tertiary amine represented by the general formula (VI):

$$NR^{12}R^{13}R^{14} \quad (VI)$$

wherein $R^{12}$, $R^{13}$ and $R^{14}$ may be the same or different and each represent a lower alkyl group.

5. The process for the preparation of a (S)-2-aralkyl-3-chloropropionic acid as in claim 1, wherein said complex of a bidentate phosphine with ruthenium is a complex represented by the general formula (X):

$$RuX_kJ_m(L) Q_n \quad (X)$$

wherein X represents a halogen atom; J represents benzene, p-cymene, a lower alkyl ester of benzoic acid, or acetonitrile; Q represents a halogen atom, $ClO_4$, $PF_6$ or $BF_4$; and L is a bidentate phosphine represented by the general formula (III):

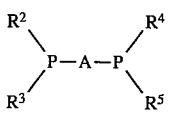

wherein $R^2$, $R^3$, $R^4$ and $R^5$ may be the same or different and each represent a phenyl group, a cyclohexyl group, a cyclopentyl group, or a substituted phenyl group substituted with a lower alkyl group, a lower alkoxy group or a halogen atom; and A is represented by the general formula (IV) or (V):

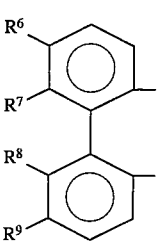

wherein $R^6$ and $R^9$ each represent a hydrogen atom; and $R^7$ and $R^8$ each represent a methyl group; or $R^6$ forms a tetramethylene group with $R^7$, and $R^8$ forms another tetramethylene group with $R^9$;

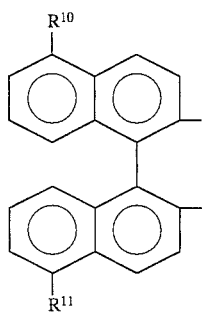 (V)

wherein $R^{10}$ and $R^{11}$ may be the same or different and each represent a hydrogen atom, an amino group, an acetylamino group, or $—SO_3M$ (in which M represents a hydrogen atom or an alkali metal atom), with ruthenium as a catalyst, in the presence of a tertiary amine represented by the general formula (VI):

$$NR^{12}R^{13}R^{14} \qquad (VI)$$

wherein $R^{12}$, $R^{13}$ and $R^{14}$ may be the same or different and each represent a lower alkyl group, with the provision that when J is a lower alkyl ester of benzene, p-cymene or benzoic acid, k is 1, m is 1 and n is 1, and when J is acetonitrile, m is 1 and n is 1 if k is 1, or m is 4 and n is 2 if k is 0.

* * * * *